(12) United States Patent
Gielkens et al.

(10) Patent No.: US 6,558,937 B1
(45) Date of Patent: May 6, 2003

(54) CELLULOSE DEGRADING ENZYMES OF ASPERGILLUS

(75) Inventors: Marcus Matheus Catharina Gielkens, Wageningen (NL); Jacob Visser, Wageningen (NL); Leendert Hendrik De Graaff, Oosterbeek (NL)

(73) Assignee: DSM N.V. (NL)

( * ) Notice: Subject to any disclaimer, the term of this patent is extended or adjusted under 35 U.S.C. 154(b) by 0 days.

(21) Appl. No.: 09/463,712

(22) PCT Filed: Jul. 31, 1998

(86) PCT No.: PCT/EP98/05047

§ 371 (c)(1),
(2), (4) Date: Apr. 4, 2000

(87) PCT Pub. No.: WO99/06574

PCT Pub. Date: Feb. 11, 1999

(30) Foreign Application Priority Data

Jul. 31, 1997 (EP) .............................................. 97202389

(51) Int. Cl.[7] .......................... C12N 9/42; C12P 19/00; A23K 1/00; A21D 2/00
(52) U.S. Cl. ........................ 435/209; 435/99; 426/622; 426/52
(58) Field of Search ................... 435/209, 99; 426/622, 426/52

(56) References Cited

U.S. PATENT DOCUMENTS

| 4,894,338 A | 1/1990 | Knowles et al. .......... 435/172.3 |
| 5,955,270 A | * 9/1999 | Radford et al. ................ 435/6 |

FOREIGN PATENT DOCUMENTS

| EP | 463 706 | 1/1992 |
| EP | 137 280 | 3/1992 |
| EP | 635 574 | 1/1995 |
| WO | 96/06935 | 3/1996 |
| WO | 97/13862 | 4/1997 |

OTHER PUBLICATIONS

Shoemaker, S., et al. (1985) Acc. No. AAP50133.*
Koch, A., et al. (1995) Acc. No Q06886.*
Takashima, S., et al. (1996) J. Bacteriol. 50, 137–147.*
Goosen et al. (1989) "Tryptophan auxotrophic mutants in *aspergillus niger*: Inactivation of the trpC gene by contransfromation mutagenesis" *Mol. Gen. Genet.* 219:282–288.
Goosen et al. 1992 "Transformation and Gene Manipulation in filamentous fungi: an overview" In:Handbook of Applied Mycology vol. 4: "Fungal Biotechnology", pp. 151–195.
Harmsen et al. (1990) "Cloning and expression of a second *Aspergillus niger* pectin lyase gene (pelA): Indications of a pectin lyase gene family in *A. Niger*" *Curr. Genet.* 18:161–166.
Murray et al. (1977) "Lamboid phages that simplify the recovery of in vitro recombinants" *Mol. Gen. Genet.* 150:53–61.
Raper and Fennell; The Genus Aspergillus, The Williams & Wilkins Company, Baltimore, pp 293–344, 1965.
Romanos et al. (1992) "Foreign gene expression in yeast: a review" *Yeast* 8:423–488.
Rosenfeld et al. (1992) "In–gel digestion of proteins for internal sequence analysis after one– or two– dimensional gel electrophoresis" *Anal. Biochem.* 203:173–179.
Saiki et al. (1988) "Printer –directed enzymatic amplification of DNA with a thermostable DNA polymerase" *Science* 239:487–491.
Visniac et al. (1957) *Bact. Rev.* 21:195–213.

* cited by examiner

Primary Examiner—Charles L. Patterson, Jr.
(74) *Attorney, Agent, or Firm*—Morrison & Foerster LLP

(57) ABSTRACT

Two cellobiohydrolase polypeptides (CBHA and CBHB) derived from Aspergillus are described and can be used to degrade cellulose. Variants of these peptides are described as well as DNA encoding the peptides, vectors and host cells. The peptides can be used to produce or process food, animal feed, wood pulp, paper and textiles.

17 Claims, 4 Drawing Sheets

CELLULOSE DEGRADING ENZYMES OF ASPERGILLUS

FIELD OF THE INVENTION

The present invention relates to polypeptides which have cellulolytic activity and which can be derived from fungae; and to polynucleotides which encode the polypeptides and vectors which can express the polypeptides in a host cell. The polypeptides can be used to degrade cellulose. In particular they can be used in the production or processing of food, animal feed, wood pulp, paper and textiles.

BACKGROUND OF THE INVENTION

Cellulose is a linear polysaccharide of glucose residues connected by beta-1,4 linkages. In nature, cellulose is usually associated with other compounds, such as hemicelluloses or lignin.

Three different classes of enzymatic activity have been shown to be required for the complete degradation of cellulose into glucose, viz. endoglucanases (EC 3.2.1.4), cellobiohydrolases (EC 3.2.1.91) and beta-glucosidases (EC 3.2.1.21).

Cellobiohydrolases attack cellulose either from the reducing or the non-reducing ends of the cellulose polymer and yield cellobiose (a glucose dimer) as the major product. Two types of cellobiohydrolase are known, cellobiohydrolase I (CBH I) and cellobiohydrolase II (CBH II). CBH I attacks cellulose from the reducing end of the cellulose polymer, and CBH II from the non-reducing end.

Cellobiohydrolase I and II from *Trichoderma reesei* have been described in EP-B-0137 280 and U.S. Pat. No. 4,894, 338, respectively. CBH I has also been identified in *Agaricus bisporus, Phanerochaete chrysosporium, Trichoderma viride* and *Humicola grisea*. Depending on both the natural origin and the previous treatment cellulose exists in many varieties differing in crystallinity, fibre composition, fibre length, fibre thickness. For fast and complete degradation of crystalline cellulose CBH and endoglucanases work synergistically (Teeri, TT., TIBTECH May 15, 1997, p. 160–167).

SUMMARY OF THE INVENTION

The invention seeks to provide novel polypeptides with CBH activity which can be used to degrade cellulose. Accordingly, the invention provides in a first aspect a polypeptide which comprises the sequence of SEQ ID No:8 (CBH A) or SEQ ID No:10 (CBH B), a sequence substantially homologous to either sequence, or a fragment of any of these sequences.

The first aspect of the invention also provides a polypeptide which is a CBH from Aspergillus.

The first aspect additionally provides a polypeptide which:
(i) has CBH activity;
(ii) has an activity of at least 50% of the maximum activity over the pH range from 3 to 5;
(iii) has an optimum activity at a temperature which is greater than 50° C.; and optionally
(iv) does not have a cellulose binding domain or a linker peptide.

A second aspect of the invention provides a polynucleotide which encodes the polypeptide of the first aspect, and a polynucleotide capable of selectively hybridising to SEQ ID No:5, 9 or a complement thereof.

A third aspect of the invention provides a vector which comprises a nucleotide of the second aspect.

A fourth aspect of the invention provides a host cell which comprises a polynucleotide or vector of the second or third aspects.

A fifth aspect of the invention provides a composition comprising a polypeptide of the invention and, for example, one or more enzyme(s).

A sixth aspect of the invention provides a use of the polypeptide or composition of the first or fifth aspects to degrade cellulose.

DETAILED DESCRIPTION OF THE INVENTION

One of the advantages of the present invention is that cellobiohydrolases may be produced which are free from endoglucanases. Since CBHs, unlike endoglucanases, do not significantly affect fibre strength they are more suitable than crude cellulase complexes for fibre modification in applications were strength is important, such as in textile and paper manufacture and finishing.

Another advantage is that the availability of cloned CBHs and endoglucanases (WO 97/13862) makes it possible to design tailor-made combinations of CBHs and endogucanases for specific applications.

Yet another advantage of the invention is that the polypeptides of the invention have optimum activity at low pH, unlike known cellobiohydrolases. Therefore, the polypeptides of the invention are well suited for use in industrial processes which are performed at low pH.

Polypeptides

The polypeptide of the invention typically has CBH activity. Generally such an activity would be the activity defined by E.C. 3.2.1.91. The term "CBH activity" includes the ability to produce cellobiose from cellulose (as a substrate).

The CBH activity may be CBH I-like activity and/or CBH II-like activity. The cellulose which is acted on by the polypeptide of the invention may be crystalline cellulose. The level of CBH activity of the polypeptide of the invention may be the same as, substantially the same as, or higher or lower than the polypeptide shown in SEQ ID No:8 or 10.

The polypeptide of the invention may or may not comprise a cellulose binding domain. Such a domain is often linked to the catalytic domain via a linker peptide in prior art CBH enzymes. Therefore if the polypeptide of the invention does not comprise a cellulose binding domain then generally it will not comprise a linker peptide either.

The polypeptide of the invention may comprise the sequence of SEQ ID No:8 or 10 or a substantially homologous sequence. The polypeptide may be 65% homologous to SEQ ID No:8 or 10, preferably 80% or 90%, and more preferably at least 95% homologous thereto over the length of SEQ ID No:8 or 10.

The polypeptide of the invention may be derived from a fungus, such as a filamentous fungus. Preferably the (filamentous) fungus is of the species Aspergillus oryzae, Aspergillus sojae, Aspergillus nidulans, species from the *Aspergillus niger* Group (as defined by Raper and Fennell, The Genus *Aspergillus*, The Williams & Wilkins Company, Baltimore, pp 293–344, 1965), specifically including but not limited to *Aspergillus niger, Aspergillus awamori, Aspergillus tubigensis, Aspergillus aculeatus, Aspergillus foetidus, Aspergillus japonicus* and *Aspergillus ficuum*.

In the context of the invention the term "derived from" includes polypeptides which naturally occur in or are produced by these fungae and therefore can be obtained from these fungae, or fragments of such polypeptides. The term also includes polypeptides which are substantially homologous (such as at least 65% homologous to SEQ ID No:8 or 10) to these naturally occurring polypeptides of the invention. Thus the invention includes polypeptides which are not naturally occurring.

The polypeptide of the invention may co-purify with an α-arabinofuranosidase (see for e.g. Example 1). The polypeptide of the invention may thus co-elute with an α-arabinofuranosidase. The α-arabinofuranosidase may be detected using the chromogenic substrate 4-methylumbelliferyl-α-L-arabinofuranoside. The α-arabinofuranosidase may be a fungal α-arabinofuranosidase, such as one from an Aspergillus species, e.g. Aspergillus niger. The α-arabinofuranosidase may be one from any of the genera or species of fungae mentioned above from which the polypeptide of the invention may be derived.

A polypeptide of the invention may comprise:
(a) a polypeptide comprising the sequence of SEQ ID No:8 or 10; or
(b) a polypeptide from Aspergillus which is a CBH or has CBH activity; or
(c) a homologue or an allelic variant of any of the polypeptides of (a) or (b) from a fungus, an Aspergillus species, from Aspergillus niger or from any of the genera or species of fungus mentioned above from which the polypeptide of the invention may be derived; or
(d) a homologue which is at least 65% homologous to (a), (b) or (c).

Methods of measuring protein homology are well known in the art and it will be understood by those of skill in the art that in the present context, homology is calculated on the basis of amino acid identity (sometimes referred to as "hard homology").

The polypeptide of the invention or fragments thereof may be used to identify cellobiohydrolases in other organisms. For example, they may be used for the production of antibodies. The sequence of the polypeptide of SEQ ID No;8 or 10 and of species homologues and allelic variants can be modified to provide polypeptides of the invention.

The modified polypeptide may retain CBH activity.

Polynucleotides

A polynucleotide of the invention may encode or comprise a sequence that encodes a polypeptide of the invention.

A polynucleotide of the invention may be capable of hybridising selectively with the coding sequence of SEQ ID No:5 or 9 or to the sequences complementary to those coding sequences. Selective hybridisation is typically achieved using conditions of medium to high stringency (for example high stringency conditions include 0.2×SSC at 60° C., and low stringency conditions include 2×SSC at 60° C.).

A nucleotide sequence capable of selectively hybridizing to the DNA coding sequence of SEQ ID No:5 or 9 or to the sequences complementary to those coding sequences will generally be at least 65%, preferably at least 80% homologous to the coding sequence of SEQ ID No:5 or 9 or their complements. Polynucleotides of the invention, which are typically provided in isolated and/or purified form, may comprise DNA or RNA. They may also be polynucleotides which include within them synthetic or modified nucleotides. For the purposes of the present invention, it is to be understood that the polynucleotides described herein may be modified by any method available in the art.

Polynucleotides such as a DNA polynucleotide and primers according to the invention may be produced recombinantly, synthetically, or by any means available to those of skill in the art.

For the recombinant production of the polypeptide of the invention a DNA sequence of the invention is used for gene amplification and/or exchange of expression signals, such as promoters, secretion signal sequences, in order to allow economic production of the polypeptide of the invention in a suitable homologous or heterologous host cell. A homologous host cell is herein defined as a host cell which is of the same species or which is a variant within the same species as the species from which the DNA sequence is derived.

Suitable host cells are preferably microorganisms like bacteria, or more preferably fungi such as yeasts or filamentous fungi. A preferred yeast host cell for the expression of a DNA sequence encoding the polypeptide of the invention is selected from the group consisting of the genera Saccharomyces, Kluyveromyces, Hansenula, Pichia, Yarrowia, and Schizosaccharomyces. More preferably a yeast host cell is selected from the group consisting of the species Saccharomyces cerevisiae, Kluyveromyces lactis (also known as Kluyveromyces marxianus var. lactis), Hansenula polymorpha, Pichia pastoris, Yarrowia lipolytica, and Schizosaccharomyces pombe.

Most preferred for the expression of a DNA sequence encoding the polypeptide of the invention are, however, filamentous fungal host cells. Preferred filamentous fungal host cells are selected from the group consisting of the genera Aspergillus, Trichoderma, Fusarium, Penicillium, Acremonium, Neurospora, Thermoascus, Myceliophtora, Sporotrichum, Thielavia, and Talaromyces. More preferably a filamentous fungal host cell is selected from the group consisting of the species Aspergillus oyzae, Aspergillus sojae, Aspergillus nidulans, species from the Aspergillus niger Group as defined by Raper and Fennell (1965, In: The Genus Aspergillus, The Williams & Wilkins Company, Baltimore, pp 293–344), specifically including but not limited to Aspergillus niger, Aspergillus awamori, Aspergillus tubigensis, Aspergillus aculeatus, Aspergillus foetidus, Aspergillus japonicus and Aspergillus ficuum, and further consisting of the species Trichoderma reesei, Fusarium graminearum, Penicillium chrysogenum, Acremonium alabamense, Neurospora crassa, Myceliophtora thermophilum, Sporotrichum cellulophilum, and Thielavia terrestris.

The expression construct can be used for transformation of the host as part of a vector carrying a selectable marker, or the expression construct is co-transformed as a separate molecule together with the vector carrying a selectable marker. Suitable selectable markers which can be used for selection of the transformed host cells are well known to the skilled person [8, 10]. Preferred markers include but are not limited to e.g. versatile marker genes that can be used for transformation of most filamentous fungi and yeasts such as acetamidase genes or cDNAs (the amdS genes or cDNAs from A.nidulans, A.oryzae, or A.niger), or genes providing resistance to antibiotics like G418 or hygromycin.

Alternatively, more specific selection markers can be used such as auxotrophic markers which require corresponding mutant host strains: e.g. URA3 (from S.cerevisiae or analogous genes from other yeasts), pyrG (from A.nidulans or A.niger) or argB (from A.nidulans or A.niger). In a more preferred embodiment, the selection marker is deleted from the transformed host cell after introduction of the expression construct in accordance with the methods described in EP-A-0 635 574, so as to obtain transformed host cells capable of producing the polypeptide which are free of selection marker genes.

For most filamentous fungi and yeast, the expression construct is preferably integrated in the genome of the host cell in order to obtain stable transformants. However, for certain yeasts also suitable episomal vector systems are available into which the expression construct can be incorporated for stable and high level expression, examples thereof include vectors derived from the 2μ and pKD1 plasmids of *Saccharomyces* and *Kluyveromyces*, respectively. In case the expression constructs are integrated in the host cells genome, the constructs are either integrated at random loci in the genome, or at predetermined target loci using homologous recombination, in which case the target loci preferably comprise a highly expressed gene. A highly expressed gene is herein defined as a gene whose mRNA can make up at least 0.5% (w/w) of the total cellular mRNA, e.g. under induced conditions, or alternatively, a gene whose gene product can make up at least 1% (w/w) of the total cellular protein, or, in case of a secreted gene product, can be secreted to a level of at least 0.1 g/l. A number of examples of suitable highly expressed genes is provided herein below.

An expression construct for a given host cell will usually contain the following elements operably linked to each other in a consecutive order from the 5'-end to 3'-end relative to the coding strand of the sequence encoding the polypeptide of the invention: (1) a promoter sequence capable of directing transcription of the DNA sequence encoding the polypeptide in the given host cell, (2) optionally, a signal sequence capable of directing secretion of the polypeptide from the given host cell into the culture medium, (3) the DNA sequence encoding a mature and preferably active form of the polypeptide, and preferably also (4) a transcription termination region (terminator) capable of terminating transcription downstream of the DNA sequence encoding the polypeptide.

A variety of promoters capable of directing transcription in the host cells of the invention is available to the skilled person [8,10]. Preferably the promoter sequence is derived from a highly expressed gene as previously defined. Examples of preferred highly expressed genes from which promoters are preferably derived and/or which are comprised in preferred predetermined target loci for integration of expression constructs, include but are not limited to genes encoding glycolytic enzymes such as triose-phosphate isomerases (TPI), glyceraldehyde-phosphate dehydrogenases (GAPDH), phosphoglycerate kinases (PGK), pyruvate kinases (PYK), alcohol dehydrogenases (ADH), as well as genes encoding amylases, glucoamylases, xylanases, cellobiohydrolases, 1-galactosidases, alcohol (methanol) oxidases, elongation factors and ribosomal proteins. Specific examples of suitable highly expressed genes include e.g. the LAC4 gene from Kluyveromyces sp., the methanol oxidase genes (AOX and MOX) from Hansenula and Pichia, respectively, the glucoamylase (glaA) genes from *A.niger* and *A.awamori*, the *A.oryzae* TAKA-amylase gene, the *A.nidulans* gpdA gene and the *T.reesei* cellobiohydrolase genes.

Preferably the polypeptide is produced as a secreted protein in which case the polynucleotide sequence encoding a mature form of the polypeptide in the expression construct is operably linked to a polynucleotide sequence encoding a signal sequence. Preferably the signal sequence is native (homologous) to the DNA sequence encoding the polypeptide. Alternatively the signal sequence is foreign (heterologous) to the DNA sequence encoding the polypeptide, in which case the signal sequence is preferably endogenous to the host cell in which the DNA sequence is expressed. Examples of suitable signal sequences for yeast host cells are the signal sequences derived from yeast a-factor genes. Similarly, a suitable signal sequence for filamentous fungal host cells is e.g. a signal sequence derived from a filamentous fungal (gluco)amylase gene, e.g. the *A.niger* glaA gene.

Downstream of the DNA sequence encoding the polypeptide, the expression construct preferably contains a 3' untranslated region containing one or more transcription termination sites, also referred to as a terminator. The origin of the terminator is less critical. The terminator can e.g. be native to the DNA sequence encoding the polypeptide. However, preferably a yeast terminator is used in yeast host cells and a filamentous fungal terminator is used in filamentous fungal host cells. More preferably, the terminator is endogenous to the host cell in which the DNA sequence encoding the polypeptide is expressed.

The recombinant host cells according to the invention may be cultured using procedures known in the art. For each combination of a promoter and a host cell, culture condition are available which are conducive to the expression the DNA sequence encoding the polypeptide. After reaching the desired cell density or titre of the polypeptide the culture may be stopped and the polypeptide may be recovered using known procedures.

In addition, homologues and allelic variants of SEQ ID No:5 or 9 may be obtained and such homologues and fragments thereof in general will be capable of selectively hybridizing to the coding sequence of SEQ ID No:5 or 9 complements.

Selective hybridisation is typically achieved under conditions of medium to high stringency (for example high stringency conditions include 0.2 SSC at 60° C., and low stringency conditions include 2×SSC at 60° C.).

Compositions containing the polypeptides

The invention also provides a composition comprising a polypeptide of the invention and, optionally, one or more enzymes. It also provides a composition comprising a recombinant host cell of the invention.

The compositions of the invention may be in a form suitable for packaging and/or storage. In a composition which comprises the polypeptide of the invention the composition is generally of a form in which the CBH activity of the polypeptide is substantially retained. The polypeptide in the composition may be attached to or mixed with a carrier, for example the polypeptide may be immobilized, such as on a solid carrier.

In a composition which comprises host cells of the invention the composition will generally be of a form which allows some or all of the host cells to remain viable. The composition may additionally comprise nutrients for the host cell, which are provided to the host cell when it is cultured.

The composition may be in a form suitable for the process in which it will be used. The composition may be formulated in any convenient way, including as a paste, liquid, emulsion, powder, flakes, granulate, pellet or other extrudate. The composition may be formulated for use in a process to produce human food, animal feed, wood pulp, paper or a textile. It may be stabilised in accordance with methods known in the art.

The composition may comprise additional substances which aid the cellulose degrading activity of the composition. Thus the composition may additionally comprise other enzymes. These other enzymes may be recombinant enzymes, or may have been obtained from an organism in which they occur naturally. The enzymes may have been substantially purified before addition to the composition of the invention, or they may be left substantially unpurified before being added to the composition of the invention.

Non-limiting examples of such other enzymes are endoglucanases (EC 3.2.1.4), other cellobiohydrolases (EC 3.2.1.91) β-glucosidases (EC 3.2.1.21), xylanases, pectinases, mannanases, phytases, alpha-amylase, proteases or various plant cell wall degrading enzymes.

The composition may comprise organisms (e.g. bacteria, fungae or yeast) which produce the above mentioned enzymes.

The composition may additionally comprise (particularly when being formulated for use in animal feed) one or more ionophores, oxidising agents, surfactants, rumen protected amino acids, enzyme enhancers or enzymes which may be produced naturally in the gastro intestinal tract of the animals to be fed.

Uses of the polypeptide, polynucleotide, host cell and composition

The invention provides the use of a polypeptide, host cell or composition of the invention to degrade cellulose. Thus the invention provides a method of degrading cellulose comprising contacting a polypeptide, host cell or composition of the invention with the cellulose (to be degraded).

In the method all or part of the cellulose may be degraded, for example from 0 to 20%, 20 to 40%, 40 to 50%, 50 to 70% or 70 to 100% by weight may be degraded.

The cellulose which is degraded in the method of the invention may be derived from a plant or a microorganism, or may have been synthetically produced by man. The cellulose may be in crystalline form. The cellulose may be partially or wholly derivatised, for example lignified.

The method of degrading cellulose of the invention may be part of a method for producing or processing food or beverages, animal feed, pulp, paper or textiles.

Moreover, the CBHs of the present invention, have broader pH optima than CBHs of the prior art, and are particularly well suited for use in industrial processes which are performed at low pH, where the CBHs of the prior art are less or not active. Since the CBHs are also more thermo-stable as compared with known CBHs they can be used in a much wider range of application conditions.

In accordance with the present invention, it has been found that the CBHs produced via the present invention may be used in the baking of breads. The incorporation of small amounts of CBH to the flour imparts favourable characteristics to the dough and thus to the bread itself such as an increased loaf volume and better textural characteristics such as break and shred quality and crumb quality.

CBHs either alone or in combination with other pure or crude endoglucanase containing enzyme mixtures may also be added to animal feed compositions which are rich in cellulose. When added to feeds (including silage) for ruminants or monogastric animals (eg. poultry or swine) which feeds contain cereals such as barley, wheat, maize, rye or oats or cereal by-products such as wheat bran or maize bran, or other plant materials such as soy beans and other legumes, the enzyme(s) significantly improve the break-down of plant cell walls which leads to better utilization of the plant nutrients by the animal. As a consequence, growth rate and/or feed conversion are improved.

The CBHs of the invention may also be used for the liquefaction of plant cell wall material, e.g. in the beverage industry.

Figure 1:
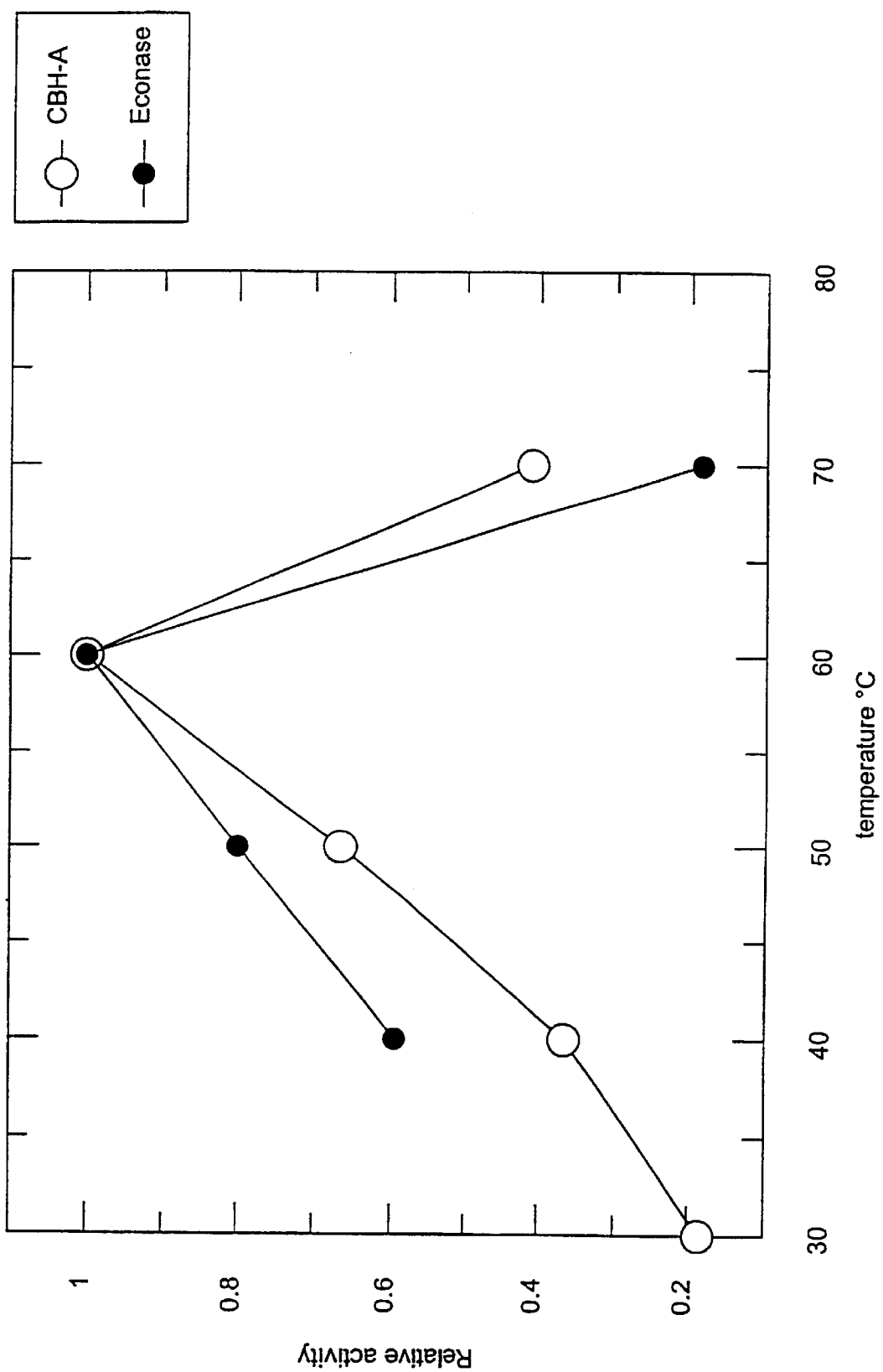
FIG. 1 shows how the activity of CBH A varies with temperature in comparison to Econase.

The invention will now be described, by way of example, by reference to the following Examples, which are not to be construed as being limiting.

EXAMPLES

Strains

E. coli LE 392[4]:

e14⁻(mcrA) hsdR514, supE44, supF58, lacY1, or D(lac1ZY)6, ga/K2, ga/T22, metB1, trpR55

Example 1

Identification of an A. niger cellobiohydrolase

A. niger N402 was grown in Aspergillus minimal medium (MM) (contains per litre: 6.0 g $NaNO_3$, 1.5 g $KH_2PO_4$, 0.5 g $MgSO_4 \cdot 7H_2O$, 0.5 g KCI, pH 6.0 and 1 ml Vishniac[7] solution (contains per litre 10 g EDTA, 4.4 g $ZnSO_4 \cdot 7H_2O$, 1.0 g $MnCl_2 \cdot 4H_2O$, 0.32 g $CoCl_2 \cdot 6H_2O$, 0.32 g $CuSO_4 \cdot 5H_2O$, 0.22 g $(NH_4)_6Mo_7O_{24} \cdot 4H_2O$, 1.47 g $CaCl_2 \cdot 2H_2O$, 1.0 g $FeSO_4 \cdot 7H_2O$, pH 4.0) supplemented with 1.5% wheat arabinoxylan. This medium was inoculated with 1×10⁶ spores per ml and mycelium was grown for 96 hours at 30° C. and 250 rpm in an orbital New Brunswick shaker. The culture filtrate was collected after filtration of the mycelium on Myracloth (nylon gauze) using a Büchner funnel and mild suction. The pH of the culture filtrate was adjusted to pH 6.0 with 0.1 M NaOH after which the culture filtrate was diluted by the addition of 2 volumes of Millipore water.

DEAE-Sephadex A-50 was equilibrated in 50 mM sodium acetate buffer pH 5.0 and was added to the culture filtrate. After 30–60 minutes of stirring at 4° C., the DEAE-Sephadex together with the culture filtrate were passed through a funnel with a glass filter holder and the DEAE-Sephadex A-50 was transferred to a column. This column was first eluted with 50 mM sodium acetate buffer pH 5.0, then with 50 mM sodium acetate buffer pH 5.0+0.5 M NaCl. Fractions containing alpha-arabinofuranosidase activity, detected using the chromogenic substrate 4-methylumbelliferyl-alpha-L-arabinofuranoside (detects alpha-arabinofuranosidases) (Sigma M-9519), were pooled and desalted by dialysis against Millipore water and subsequently dialysed against 20 mM piperazine-HCl buffer pH 5.0. After dialysis the sample was loaded on a DEAE-Sepharose Fast Flow column, this column was first eluted with 3 volumes 20 mM piperazine-HCl buffer pH 5.0 and then with a linear gradient of 0.5 M NaCl in 20 mM piperazine-HCl buffer pH 5.0. Detection of the eluted protein was performed by continuous measurement of the UV absorption at 280 nm. Fractions of 10 ml were collected which were assayed for activity of alpha-arabinofuranosidase on para-nitrophenyl-alpha-L-arabinofuranoside (PNP-A)(Sigma N-3641) the a-arabinofuranosidase activity was found in fractions 11–27, 41–47 and 52–61. Fractions 41–47 were pooled and subsequently dialysed against 100 mM piperazine-HCl buffer pH 5.0 and the whole sample (200 ml) was loaded on a DEAE Sepharose FF column (Pharmacia) to concentrate the protein to a single peak using a 1 M NaCl gradient in 200 mM piperazine-HCl pH 5.0 buffer. Protein containing fractions were pooled (20 ml) and were first dialysed against Millipore water, then against 20 mM piperazine-HCl pH 5.0 and finally concentrated using a Speed Vac concentrator to 6 ml. This preparation was loaded on a Sephacryl S-300 column, which was eluted with 20 mM piperazine-HCl pH 5.0, 0.1 M NaCl. Fractions having activity on PNP-A were pooled, dialysed against 10 mM piperazine-HCl pH 5.0 and concentrated in a Speed Vac concentrator to 2 ml. This sample was then loaded on a Superdex 75 (Hiload column 16/60) (Pharmacia) column, which was equilibrated and eluted with 20 mM piperazine-HCl pH 5.0, 0.1 M NaCl. Fractions having a-arabinofuranosidase activity were dialysed against 10 mM Na-acetate buffer pH 3.5. The final purification was done on a Mono S cation exchange column (HR 5/5, Pharmacia). The column was equilibrated with 10 mM Na-acetate buffer pH 3.5 buffer in which the sample was loaded. Protein was eluted using 27 ml of a linear gradient 1 M NaCl in 10 mM Na-acetate buffer pH 3.5. The enzyme eluted at about 100 mM NaCl.

The purified enzyme was sent to EUROSEQUENCE (Groningen, The Netherlands). There it was applied to an SDS-PAGE gel and internal sequence analysis of the protein was performed essentially as described in reference 11.

Amino acid sequences were performed using an automated sequencer (Model 477A, Applied Biosystems) coupled to an HPLC (Model 120A ABI) for analysis of the phenylthiodantoin (PTH) amino acids. The following internal sequences were determined:

Leu-Tyr-Leu-Met-Ser-Asp-Asp -Ser-Asn-Tyr-Glu-Leu-Phe-Lys
(SEQ ID No:1)

Leu-Gly-Asn-Thr-Asp-Phe-Tyr-Gly-Pro-Gly-Leu-Thr-Val-Asp-Thr-Asn-Ser-Pro-Ph e -Thr-Val-Val-Thr-Gln
(SEQ ID No:2)

Surprisingly, the partial amino acid sequence of one of the internal fragment of the isolated enzyme (SEQ ID No:1) showed a very high identity with *Agaricus bisporus* CBH I, i.e. 11 out of 13 residues were identical. This was the first indication of cellobiohydrolase genes in *Aspergillus*.

Example 2

Isolation of cDNA clones coding for *A. niger* cellobiohydrolase

Example 2.1

Generation of probe

The Agaricus bisporus CBH I enzyme is encoded by the ce/2 gene (EMBL Acc. No. Z50094). The two following oligonucleotides were designed to PCR the coding region of ce/2:

5'-GTC GGT ACC AAC ATG GCC G-3' (19-mer)
(SEQ ID No:3)

5'-ACT CAG AAA CAT TGG CTA TAG-3' (21-mer)
(SEQ ID No:4)

These oligo nucleotides, as depicted in SEQ ID NOS.3 and 4, were used in PCR using plasmid DNA containing Agaricus bisporus ce/2 sequences as a template[5].

For a PCR 2 ng of plasmid DNA was combined with 5 µl 10x reaction buffer (200 mM Tris-HCl, pH 8.4; 500 mM KCl); 3 µl 50 mM $MgCl_2$; 4.0 µl 1.25 mM of each of the four deoxynucleotide triphosphates and 50 pmol of the oligonucleotides in a final volume of 50 µl. The reaction mixture was mixed and 0.5 µl TAQ polymerase (5U/µl) (Life Technologies) was added. The DNA was heat denatured by incubation for 5 minutes at 95° C. followed by 25 cycles of 1 minute at 95° C., 1 minute at 52° C. and 1 minute at 72° C. After these 25 cycles the mixture was incubated for 5 minutes at 72° C. Analysis of the reaction products revealed one discrete product of 1.5 kb, which was the expected size.

Example 2.2

$^{32}$P-labelling of 1.5 kb PCR fragment

The 1.5 kb fragment obtained by PCR was isolated and labelled as described in EP-A-0 463 706, Examples 2.2 and 7.1.

Example 2.3

Screening of the *A. niger* N400 cDNA library for cellobiohydrolase cDNA clones

The construction of the *A. niger* cDNA library is described in WO 96/06935 (Example 3).

To screen the *A. niger* N400 cDNA library for cbh cDNA clones, $5 \times 10^3$ pfu per plate were plated in NZYCM topagarose containing 0.7% agarose on 85-mm-diameter NZYCM (1.5% agar) plates as described in reference 3, using *E. coli* LE392 as plating bacteria.

After overnight incubation of the plates at 37° C. two replicas of each were made on HybondN filters (Amersham) as described in reference 3.

The filters were prehybridized at 65° C. for 2 hours in prehybridization buffer containing; 6xSSC, 0.5% SDS, 5xDenhardt's solution, 0.01 M EDTA and 100 µg/ml heat denatured herring sperm DNA (Boerhinger Mannheim). After two hours prehybridization, the prehybridization buffer was replaced by hybridization buffer which was identical to the prehybridization buffer, but contained the $^{32}$P labelled 1.5 kb PCR fragment containing *Agaricus bisporus* ce/2 sequences and prepared as described in Example 2.2. The filters were hybridized for 18 hours at a temperature of 60° C.

After hybridization the filters were first washed at 60° C. for 30 minutes in 4xSSC/0.5% SDS followed by two washing steps at 60° C. for 30 minutes in 2xSSC/0.5% SDS. The air dried filters were taped on a sheet of Whatman 3MM paper, keying marks were made with radioactive ink and the Whatman paper and filters were covered with Saran Wrap. Hybridizing plaques were identified by exposure of Kodak XAR X-ray film for 72 hours at -70° C. using an intensifying screen.

About fifty positive hybridizing plaques, appearing in duplicate were found per plate. Twelve positive plaques were picked from the plate using a Pasteur pipette and the phages were eluted from the agar plug in 1 ml of SM buffer containing 20 µl chloroform, as described in reference 3. The phages obtained were purified by repeating the procedure described above using filter replicas from plates containing 50–100 plaques of the isolated phages.

After purification the phages were propagated by plating $5 \times 10^3$ phages on NZYCM medium. After overnight incubation at 37° C. confluent plates were obtained, from which the phages were eluted by adding 5 ml SM buffer and storing the plate for 2 hours at 4° C. with intermittent shaking. After collection of the supernatant using a pipette, the bacteria were removed from the solution by centrifugation at 4,000x g for 10 minutes at 4° C. To the supernatant 0.3% chloroform was added and the number of pfu was determined. These phage stocks contain approximately $10^7$ pfu/ml.

Example 2.4

Restriction analysis of cbh cDNA clones

The recombinant Uni-ZAP XR clones containing cbh cDNA were converted to Bluescript phagemids by superinfection with the filamentous helper phage ExAssist™, which is included in the ZAP™-cDNA synthesis kit from Stratagene, according to the manufacturer's instructions.

The phagemid DNA was subsequently isolated as described in reference 6.

The isolated DNA of eight cbh cDNA clones were subjected to restriction analysis using the following restriction enzymes: EcoRI and XhoI. The DNA was digested for 2 hours at 37° C. in a reaction mixture composed of the following solutions; 2 µl (>>1 mg) DNA solution; 2 µl of the appropriate 10x React buffer (Life Technologies); 10 U of each Restriction enzyme (Life Technologies) and sterile distilled water to give a final volume of 20 µl. After addition of 4 µl DNA loading buffer the samples were loaded on a 0.7% TAE-agarose gel. The DNA fragments were separated by electrophoresis at 80 V for 1.5 hours. The restriction analysis of the isolated cDNA clones revealed two types of plasmid; one containing inserts of 1.2 kb, the other inserts of 1.8 kb.

Example 2.5

Sequence analysis of A. niger cbh cDNA clone CBHA-C9

The sequence of the *A. niger* cbh cDNA clones was determined by subcloning fragments from one of the positive clones of Example 2.4 with 1.8 kb insert, called CBHA-C9, in pBluescript SK⁻. Sequencing reactions were conducted using the ThermoSequenase fluorescent labelled primer cycle sequencing kit (Amersham) with universal sequencing primers. The sequencing reactions were analysed on an ALFexpress sequencer (Pharmacia). Sequence analysis was performed using the Winstar programme (LaserGene) and yielded the sequence as shown in SEQ ID No:5. The amino acid sequence of the coding region, corresponding to nucleotides 49 to 1404, is shown in SEQ ID No:8. The coding region encodes the mature enzyme (amino acid 18 to 452) plus its pre-sequence (amino acid 1 to 17). The protein does not contain a linker peptide, nor a cellulose binding domain.

Example 2.6

Screening of the A. niger genomic library for the cbhA gene

For the screening of the *A. niger* genomic library, constructed as described in reference 2, for the cbhA gene 3×10³ pfu per plate were plated in NZYCM top-agarose containing 0.7% agarose on five 85-mm-diameter NZYCM (1.5% agar) plates as described in reference 3, using *E. coli* LE392 as plating bacteria.

After overnight incubation of the plates at 37° C. two replicas of each were made on HybondN filters (Amersham) as described in reference 3.

The filters were prehybridized at 68° C. for two hours in prehybridization buffer containing; 6xSSC, 0.5% SDS, 5xDenhardt's solution, 0.01 M EDTA and 100 µg/ml heat denatured herring sperm DNA (Boerhinger Mannheim). After two hours prehybridization, the prehybridization buffer was replaced by hybridization buffer which was identical to the prehybridization buffer, but contained the $^{32}P$ labelled the 1.8 kb insert from cDNA clone CBHA-C9 and prepared as described in Example 2.2. The filters were hybridized for 18 hours at an temperature of 68° C.

After hybridization the filters were first washed at 68° C. for 30 minutes in 4xSSC/0.1% SDS followed by a second wash at 68° C. during 30 minutes in 2xSSC/0.1% SDS. The filters were then washed twice at 68° C. for 30 minutes with 0.1xSSC/0.1% SDS. The air dried filters were taped on a sheet of Whatman 3MM paper, keying marks were made with radioactive ink and the Whatman paper and filters were covered with Saran Wrap. Hybridizing plaques were identified by exposure of Kodak XAR X-ray film for 72 h at −70° C. using an intensifying screen.

Two to three positive hybridizing plaques, appearing in duplicate were found per plate. Five positive plaques were picked from the plate using a Pasteur pipette and the phages were eluted from the agar plug in 1 ml of SM buffer containing 20 µl chloroform, as described in reference 3. The phages obtained were purified by repeating the procedure described above using filter replicas from plates containing 50–100 plaques of the isolated phages.

Example 3

Cloning of further A. niger cbh cDNA

Example 3.1

Generation of probe

The partial amino acid sequences of the internal fragments of the cellobiohydrolase which resulted from the arabinofuranosidase purification (SEQ ID No:1 and 2), were used to design oligonucleotide mixtures. The following mixtures were derived:

5'-GAY GAY AGY AAY TAY GAR TTR TTY AA-3' (26-mer)
(SEQ ID No:6)
5'-GTR AAN GGR CTR TTN GTR TC-3' (20-mer)
(SEQ ID No:7)

in which R stands for an A or G; Y for a C or T and N for any base. The oligonucleotide depicted in SEQ ID No:6 was derived from the amino acid sequence depicted in SEQ ID No:1, as described in Example 1 from amino acid 6 (D) to amino acid 14 (K). The oligonucleotide depicted in SEQ ID No:7 was derived from the amino acid sequence depicted in SEQ ID No:2, as described in Example 1 from amino acid 20 (T) to amino acid 14 (D).

These oligo nucleotides were used in PCR using excised plasmid DNA from the *A. niger* N400 cDNA library as a template[5].

The TaqBead™ PCR kit (Promega) was used for PCR, i.e. 5 ng of plasmid DNA was combined with 5 µl 10* reaction buffer, 6 µp 25 mM MgCl₂, 8 µl 1.25 mM of each of the four deoxynucleotide triphosphates and 50 pmol of the oligonucleotides depicted in SEQ ID NO's:6 and 7 in a final volume of 50 µl. The reaction mixture was mixed and 0.5 µl TAQ polymerase (5 U/µl) (Life Technologies) was added. The DNA was heat denatured by incubation for 5 minutes at 95° C. followed by 24 cycles of 1 minute at 94° C., 1.5 minute at 48° C. and 1.5 minute at 72° C., in which the annealing temperature was lowered every cycle by 0.3° C. This was followed by 10 cycles of 1 minute at 94° C., 1.5 minute 40° C. and 1.5 minute 72° C. After these 10 cycles the mixture is incubated for 5 minutes at 72° C. Analysis of the reaction products revealed one discrete product of approximately 450 bp.

Example 3.2

$^{32}$P-labelling of 450 bp PCR fragment

The 450 bp fragment obtained by PCR was isolated and labelled as described in EP-A-0 463 706, Examples 2.2 and 7.1.

Example 3.3

Screening of the *A. niger* N400 cDNA library for further cbh cDNA clones

The construction of the *A. niger* cDNA library is described in WO 96/06935 (Example 3).

To screen the *A. niger* N400 cDNA library for further cbh cDNA clones, 5 * 10$^3$ pfu per plate were plated in NZYCM topagarose containing 0.7% agarose on 85-mm-diameter NZYCM (1.5% agar) plates as described reference 3, using *E. coli* LE392 as plating bacteria.

Hybridization was performed as described in Example 2.6, using the 450 bp PCR fragment prepared as described in Example 3.2

About ten to twenty positive hybridizing plaques, appearing in duplicate on the replica filters were found per plate. Eight positive plaques were picked from the plate using a Pasteur pipette and the phages were eluted from the agar plug in 1 ml of SM buffer containing 20 µl chloroform, as described in reference 3. The phages obtained were purified by repeating the procedure described above using filter replicas from plates containing 50–100 plaques of the isolated phages.

After purification the phages were propagated by plating 5×10$^3$ phages on NZYCM medium. After overnight incubation at 37° C. confluent plates were obtained, from which the phages were eluted by adding 5 ml SM buffer and storing the plate for 2 hours at 4° C. with intermittent shaking. After collection of the supernatant using a pipette, the bacteria were removed from the solution by centrifugation at 4,000x g for 10 minutes at 4° C. To the supernatant 0.3% chloroform was added and the number of pfu is determined. These phage stocks contain approximately 10$^7$ pfu/ml.

Example 3.4

Restriction analysis of further cbh cDNA clones

The recombinant Uni-ZAP XR clones containing cbh cDNA were converted to Bluescript phagemids by superinfection with the filamentous helper phage ExAssist™, which is included in the ZAP™-cDNA sysnthesis kit from Stratagene, according to the manufactures instructions.

The phagemid DNA was subsequently isolated as described in reference 6.

The isolated DNA of eight cbh cDNA clones were subjected to restriction analysis using the following restriction enzymes: EcoRi and Xhol. The DNA was digested for 2 hours at 37° C. in a reaction mixture composed of the following solutions; 2 µl (>>1 µg) DNA solution; 2 µl of the appropriate 10x React buffer (Life Technologies); 10 U of each Restriction enzyme (Life Technologies) and sterile distilled water to give a final volume of 20 µl. After addition of 4 µl DNA loading buffer the samples were loaded on a 0.7% TAE-agarose gel. The DNA fragments were separated by electrophoresis at 80 V for 1.5 hours. The restriction analysis revealed that these further cbh cDNA clones, called cbhB clones, had an insert size of approximately 1.8 kb.

Example 3.5

Sequence analysis and description of *A. niger* cbh cDNA clone CBHB-C13

The sequence of the *A. niger* cbh cDNA clones was determined by subcloning fragments from one of the positive clones of Example 3.4 with 1.8 kb insert, called CBHB-C3$^-$. Sequencing reactions were conducted using the ThermoSequenase fluorescent labelled primer cycle sequencing kit (Amersham) with universal sequencing primers. The sequencing reactions were analyzed on an ALFexpress sequencer (Pharmacia). Sequence analysis was performed using the Winstar programme (LaserGene) and yielded a nucleotide sequence consisting of 1781 nucleotides as shown in SEQ ID No:9, cDNA CBHB-C13. Clone CBHB-C13 contains one open reading frame from nucleotide 28 up to and including nucleotide 1635. The encoded protein consists of 536 amino acids (SEQ ID No:10, CBHB), with a calculated mass of 56,226 Da. The protein contains three domains: a catalytic domain from amino acid 22 up to and including amino acid 460; a linker peptide from amino acid 461 up to and including 500 and a cellulose binding domain (CBD) from amino acid 501 up to and including amino acid 536. After removal of the pre-sequence of 21 amino acids from the N-terminus, the mature protein consists of 515 amino acids with a calculated mass of 53,989 Da and a calculated isoelectric point of 3.9.

Example 4

Expression of cbhA cDNA in *A. niger*

Example 4.1

Construction of a cbhA expression cassette

The cDNA clone CBHA-C9 of Example 2.5 was used to construct an expression plasmid. All digestions were conducted using 1–3 µg DNA, 2 µl of the appropriate 10x React buffer (Life Technologies), 10 U Restriction enzyme (Life Technologies) and sterile distilled water to give a final volume of 20 µl. Digestions were incubated at 37° C. for 1–2 hours. The digested samples were loaded on a 0.7% agarose gel in TAE buffer and the DNA fragments were subsequently separated by electrophoresis at 80 V. After electrophoresis the appropriate band was sliced out and the DNA fragment was isolated using the GeneClean™ kit (Biogel 101 Inc.), according to the manufacturers instructions. Ligations were performed in 10x ligation buffer (Promega), 50–100 ng vector DNA, a 3-fold molar excess of insert DNA, 1 U T4-Ligase resulting in a final volume of 10 µl. After incubation overnight at 15° C., 4 µl of the mixture was used to transform *E. coli* DH5a competent cells prepared as follows: 200 µl of an *E. coli* DH5a overnight culture pregrown in LB medium (LB medium per 1000 ml: 10 g trypticase peptone (Life Technologies), 5 g yeast extract (Life Technologies), 10 g NaCl, 0.5 mM Tris-HCl pH 7.5). This culture was incubated in an orbital shaker at 37° C. until its density corresponds to an O.D.600 of 0.15–0.2. The bacteria were then collected by centrifugation at 3000 rpm at 4° C. After discarding the supernatant the cells were kept on ice constantly. The bacterial pellet was washed in 40 ml K-MES transfer buffer (per 100 ml: 6 ml 1 M CaCl$_2$, 0.5 ml 1 M MgCl$_2$, 4 ml 0.5 M K-MES pH 6.0, 0.5 ml 1 M MnCl$_2$) by resuspending these cells followed by centrifugation as described above. Finally the cells were resuspended in 10 ml K-MES/ glycerol (=K-MES transfer buffer+15% glycerol). Aliquots (50 µl) were either used immediately for transformation or frozen at −70° C.

*E. coli* DH5a competent cells were used in transformation experiments by combining 50 µl of the cells suspension with 4.5 µl of the ligation mixture. After a 30 minute incubation period on ice, the cells were incubated for 2 minutes at 42° C. Then 1 ml LB medium was added and the cells were incubated at 37° C. for 1 hour. The bacteria were then collected by centrifugation at 14,000 g for 20 seconds after discarding the supernatant the cells were resuspended in 100 µl LB medium. The resulting bacterial suspension was plated on LB medium containing 100 µg/ml ampicillin and 50 µg/ml X-gal and 60 µg/ml IPTG in case of blue/white screening.

A selection of 2–12 of the resulting colonies were grown overnight in LB medium containing 100 µg/ml ampicillin. From the cultures plasmid DNA was isolated by the alkaline lysis method as described in reference 3, which was used in restriction analysis as described in Example 2.4 to select a clone harboring the desired plasmid.

The above described methods were used to construct the cbhA expression plasmid designated as pIM3006. The plasmid promH, containing the *A. niger* pkiA promoter, was digested with Sstl and Nsi1 and ligated into Sstl-Nsi1 digested pCBHA-C9. After linearization of the resulting plasmid, which contains the pkiA-cbhA fusion, using Sstl, this construct was partial digested using Bg/ll. The 2.4 kb Sstl-Bg/ll fragment was ligated into a BamHI-Sstl digested plasmid carrying a BamHI-Hindlll fragment containing the terminator of the *Aspergillus nidulans* trpC gene. The Bg/ll restriction site lies approximately 150 bp downstream the putative stop codon. The resulting construct is designated as pIM3006.

Plasmid DNA was isolated on a large scale from 100 ml cultures *E. coli* DH5a containing the final expression plasmid pIM3006 grown in LB medium containing 100 µg/ml ampicillin using the Nucleobond PC-100 kit (Nagel) according to the manufacturers instructions.

Example 4.2

Introduction of the cbhA expression construct in *A. niger* by cotransformation and screening of transformants for the expression of the *A. niger* cbhA gene The plasmid pIM3006, obtained in Example 4.1 was introduced in *A. niger* by cotransformation using the *A. niger* pyrA as a selective marker on the plasmid pGW635 (Goosen et al., 1989) and the plasmid pIM3006 as the cotransforming plasmid.

Protoplasts were prepared from mycelium by growing *A. niger* on minimal medium supplemented with 0.5% yeast extract, 0.2% casamino acids, 50 mM glucose, 1.5 mM leucine and 10 mM uridine for 18 hours at 30° C. The preparation of protoplasts of *A. niger* and the transformation procedure was performed as described in reference 8. The resulting PYR$^+$ transformants were analyzed for the expression of the *A. niger* cbhA gene by SDS-PAGE.

The transformants were analyzed for the formation of the *A. niger* cbhA gene product, the CBHA protein. Twelve of these transformants were used in a growth experiment to analyze for CBHA expression. The transformants were grown in 50 ml minimal medium (per litre medium: 15 g $KH_2PO_4$, 0.5 g KCl, 0.5 g $MgSO_4.7H_2O$, 6 g $NaNO_3$, 1 ml Vishniac solution[7] ( pH 6.0) containing 4% D-fructose, 0.1% yeast extract and 1.5 mM leucine for 30 hours at 30° C. After growth, the mycelium was removed by filtration and the culture filtrate was analyzed by SDS-PAGE. Transformant *A. niger*: pIM3006-55 was the best CBHA producer (approx. 20 µg ml$^{-1}$).

Example 4.3

Purification of the CBHA enzyme

A 1 l Erlenmeyer flask containing 300 ml medium (per litre medium: 4 g $NH_4Cl$, 1.5 g $KH_2PO_4$, 0.5 g KCl, 0.5 g $MgSO_4.7H_2O$, 1 ml Vishniac salts solution (contains per litre 10 g EDTA, 4.4 g $ZnSO_4.7H_2O$, 1.0 g $MnCl_2.4H_2O$, 0.32 g $CoCl_2.6H_2O$, 0.32 g $CuSO_4.5H_2O$, 0.22 g $(NH_4)_6Mo_7O_{24}.4H_2O$, 1.47 g $CaCL_2.2H_2O$, 1.0 g $FeSO_4.7H_2O$, pH 4.0 (Vishniac and Santer, 1957), pH 5.0) supplemented with 0.2% ultrafiltrated yeast extract (Life Technologies), 0.5% casamino acids (Life Technologies), 10 mM leucine and 5% sucrose as C-source) was inoculated with 2–10$^9$ spores of strain *A. niger*: pIM3006-55 and grown for 6 hours at 30° C. This entire culture was then added to 1.7 litre medium in an Applikon 3 litre fermentor (BTSO6) which was controlled by a Bioprocessor unit ADI 1020 (Applikon). The fermentation was temperature controlled at 30° C. and the pH was allowed to drop to pH 3.0 at which it was maintained by addition of 5N NaOH. 1.9 litre culture broth was drained from the fermentor 30 hours after inoculation. The mycelia was separated from the culture broth by filtration. The fermentor was filled again with 2 litre of fresh culture medium and cultured for another 30 hours as described above. After this second run the mycelia was separated from the culture broth by filtration. The culture filtrates from the both runs were combined and piperazine was added to a final concentration of 10 mM. The pH was adjusted to pH 5.5 with 10 N NaOH. The culture filtrate was then applied on a Streamline™ anion exchange column (Pharmacia). After loading, the column was washed with 10 mM piperazine-HCl (pip-HCl) pH 5.5. The enzyme was eluted from the column by applying a salt pulse using 10 mM pip-HCl pH 5.5/1 M NaCl. Fractions of 15 ml were collected and CBH activity was detected using the chromogenic substrate 4-methylumbelliferryl-b-D-cellobioside (detects cellobio-hydrolases)(Sigma M-6018). The majority of the CBH activity was present in the fractions 2, 3 and 4. These fractions were pooled and dialysed against 10 mM pip-HCl pH 5.5.

Example 4.4

Influence of pH and temperature of the CBHA enzyme

Enzyme purified as described in Example 4.3 was used for characterization of the enzyme activity. A commercially available CBHI-containing Trichoderma enzyme preparation: Econase CEP (ALKO) was used as a reference enzyme. The assay for the determination of cellobiohydrolase activity is based on the property of the enzyme to hydrolyse p-nitrophenyl-β-D-cellobioside.

To determine the influence of the temperature on the enzyme activity 25 µl enzyme solution was added to 225 µl of a solution containing 0.1% p-nitrophenyl-β-D-cellobioside and 25 mM gluconolactone in a 50 mM sodium acetic acid buffer at pH 5.0. Following an incubation of 15 minutes at 30, 40, 50, 60 or 70° C. the enzyme activity was stopped by adding 750 µl of a 0.5 M glycine buffer pH 9.0. The concentration of p-nitrophenol formed was determined spectrophotometrically at 400 nm.

In FIG. 1 it can be seen that under these assay conditions the temperature optimum of the enzyme is 60° C. Econase also has a temperature optimum at 60° C., but the remaining activity at 70° C. of CBHA is 40%, whereas the Econase activity at that temperature is less than 10 % of the maximum activity.

To determine the pH optimum of CBHA the assay as described above was performed at 40° C., using 100 mM sodium citric acid buffer, set at different pH values. The activity was measured at pH-values ranging from 2.5 up to 6.5.

Figure 2:
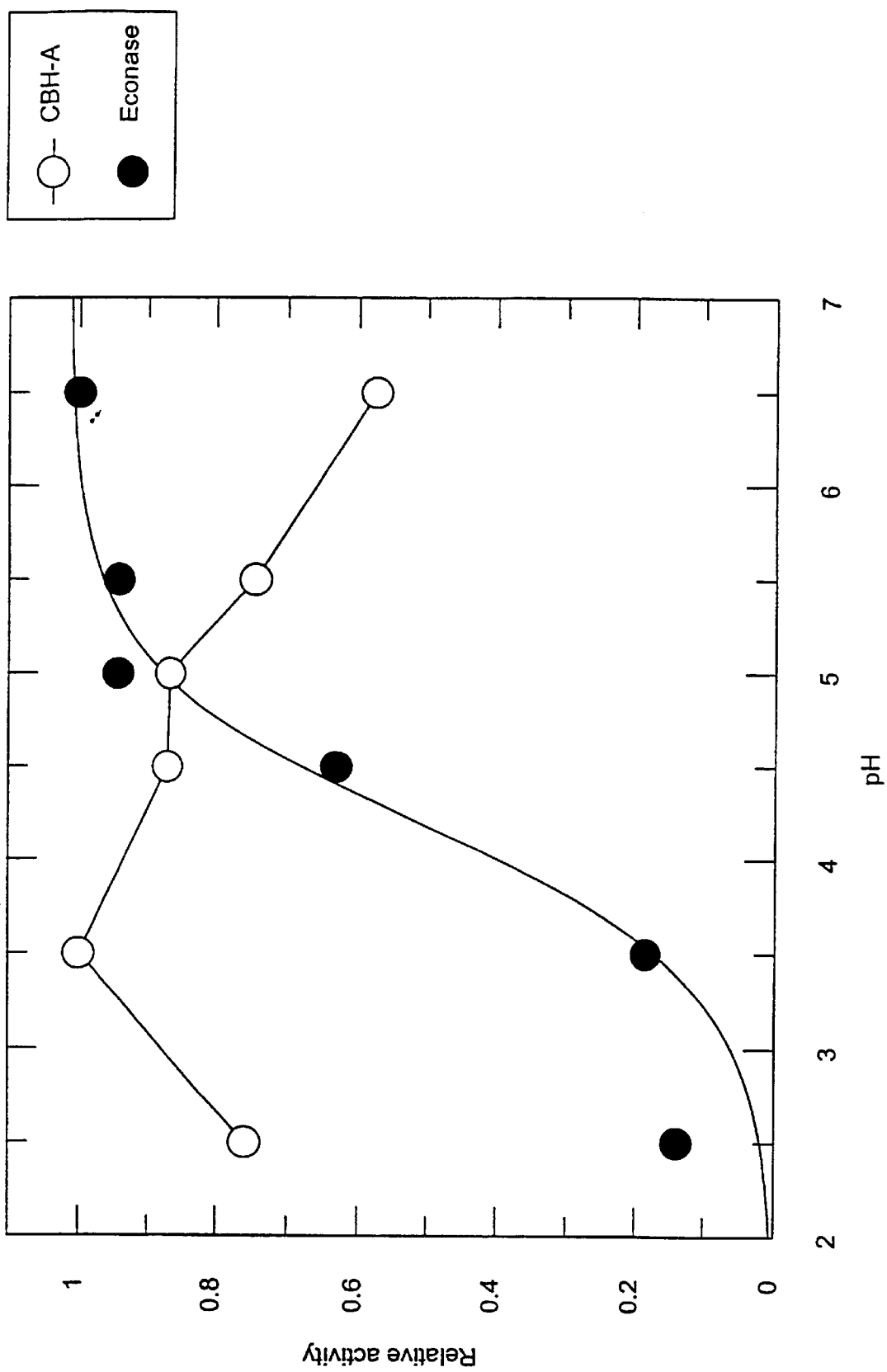
FIG. 2 shows how the activity of CBH A varies with pH in comparison to Econase.

In FIG. 2 it can be seen that the pH profile of CBHA is completely different from the pH profile of Econase. CBHA has more than 50% activity at the whole range from 2.5 to 6.5, whereas below pH 4.5 the Econase activity decrease to below 50%.

Example 5

Expression of cbhB cDNA in *A. niger*

Example 5.1

Construction of a cbhB expression cassette

The cDNA clone CBHB-C13 of Example 3.4 was used to construct an expression plasmid. To introduce a NsiI restriction site at the ATG codon, a PCR was conducted using the following oligo nucleotides:

5'-CAC AAT GCA TTC CTT CCA AAT CTA CCG-3' (27-mer)
(SEQ ID No:11)
5'-CAC CGT CAG CGT CCA TGG CG-3' (20-mer)
(SEQ ID No:12)

These oligo nucleotides were used in PCR using CBHB-C13 DNA as template[5]. For a PCR 5 ng of CBHB-C13 DNA was combined with 2.5 µl 10x reaction buffer (200 mM Tris-HCl (pH 8.4), 500 mM KCl); 0.75 µl 50 mM Mg2Cl; 4 µl dNTPs (1.25 mM each); 25 pmol of each oligo nucleotide and 0.2 U Taq polymerase (Life Technologies). The 530 bp PCR product was ligated into a pGEM-T vector (Promega) according to the manufactures instructions, resulting in plasmid pMK49. Plasmid DNA was isolated by the alkaline lysis method[6]. Nucleotide sequence analysis was conducted as described in Example 2.5. A 530 bp SstI/NcoI fragment was isolated from plasmid pMK49 and ligated into a 4.4 kb SstI/NcoI fragment isolated from plasmid CBHB-C13 resulting in pLIG418. All DNA manipulations were conducted as described in Example 4.1.

To introduce a BamHI restriction site directly downstream the stop codon, a PCR was conducted using the following oligo nucleotides:

5'-CCT AGG ATC CTA CAA ACA CTG CGA GTA GTA C-3' (31-mer)
(SEQ ID No:13)
5'-GTT AAC TCG TCG GCC TCG-3' (18-mer)
(SEQ ID No:14)

PCR was conducted as described above. The 340 bp PCR product was ligated into a pGEM-T vector (Promega), resulting in plasmid pMK51. After the sequence analysis, a 0.4 kb SphI/BamHI fragment was isolated from plasmid pMK51 and ligated into pUC18, which was linearized using SphI and BamHI. This resulted in plasmid pLIG420. A 350 bp KpnI/HpaI fragment was isolated from plasmid pLIG420 and ligated into a 4.45 kb fragment isolated from pLIG418, resulting into pLIG423.

The plasmid promH, containing the *A. niger* pkiA promoter, was digested with SstI and NsiI to obtain a 0.75 kb fragment which was ligated into SstI-NsiI digested pLIG423. The resulting plasmid pLIG425, which contains the pkiA-cbhB fusion, was digested with BamHI and a 2.4 kB fragment was isolated. This fragment was ligated into a with BamHI linearized plasmid carrying a BamHI-HindIII fragment containing the terminator of the Aspergillus nidulans trpC gene. The resulting construct is designated as pIM3011.

Plasmid DNA was isolated on a large scale from 100 ml cultures *E. coli* DH5a containing the final expression plasmid pIM3011 grown in LB medium containing 100 µg/ml ampicillin using the Nucleobond PC-100 kit (Nagel) according to the manufacturers instructions.

Example 5.2

Introduction of the cbhB expression construct in *A. niger* by cotransformation and screening of transformants for the expression of the *A. niger* cbhB gene The plasmid pIM3011, obtained in Example 5.1 was introduced in *A. niger* by cotransformation using the *A. niger* pyrA as a selective marker on the plasmid pGW635 (Goosen et al., 1989) and the plasmid pIM3011 as the cotransforming plasmid. The transformation procedure and screening of CBHB producing strains was performed as described in Example 4.2.

Transformant *A. niger*: pIM3011–34 was the best CBHB producer.

Example 5.3 Purification of the CBHB enzyme

Twelve 1 l Erlenmeyer flasks containing 250 ml medium (per litre medium: as described in Example 4.3 with 7% D-glucose in stead of 5% sucrose) were inoculated with $2\times10^6$ spores per ml medium of strain *A. niger*: pIM3011–34 and grown for 30 hours at 30° C. After growth, the mycelia was separated from the culture broth by filtration and 4-methylpiperazine was added to a final concentration of 20 mM. The pH was adjusted to pH 4.5 with 10 N NaOH. The culture filtrate was then applied on a Streamline™ anion exchange column (Pharmacia). After loading, the column was washed with 20 mM 4- methylpiperazine-HCl (pip-HCl) pH 4.5. The enzyme was eluted from the column by applying a salt pulse using 20 mM 4-methylpiperazine-HCl pH 4.5/1 M NaCl. Fractions of 25 ml were collected and CBH activity was detected using the chromogenic substrate 4-methylumbelliferryl-b-D-cellobioside (detects cellobiohydrolases)(Sigma M-6018). The majority of the CBH activity was present in the fractions 2, 3 and 4. Fractions containing cellobiohydrolase activity were pooled and dialyzed against 20 mM 4-methylpiperazine pH 4.5. Half of the enzyme solution was applied on a Resource30Q column (Pharmacia), washed with 20 mM 4-methylpiperazine-HCl pH 4.5, and eluted from the column using a 0–0.5 M NaCl gradient in 20 mM 4-methylpiperazine-HCl buffer pH 4.5. Fractions containing cellobiohydrolase activity on the chromogenic substrate 4-methylumbelliferryl-b-D-cellobioside were pooled.

Example 5.4

Influence of pH and temperature of the CBHB enzyme

Enzyme purified as described in Example 5.3 was used for characterization of the enzyme activity. A commercially available CBHI-containing Trichoderma enzyme preparation: Econase CEP (ALKO) was used as a reference enzyme. The assay for the determination of cellobiohydrolase activity is based on the property of the enzyme to hydrolyse p-nitrophenyl-β-D-cellobioside.

To determine the influence of the temperature on the enzyme activity 25 µl enzyme solution was added to 225 µl of a solution containing 0.1% p-nitrophenyl-β-D-cellobioside and 25 mM gluconolactone in a 50 mM sodium acetic acid buffer at pH 5.0. Following an incubation of 15 minutes at 30, 40, 50, 60 or 70° C. the enzyme activity was stopped by adding 750 μl of a 0.5 M glycine buffer pH 9.0. The concentration of p-nitrophenol formed was determined spectrophotometrically at 400 nm.

Figure 3:
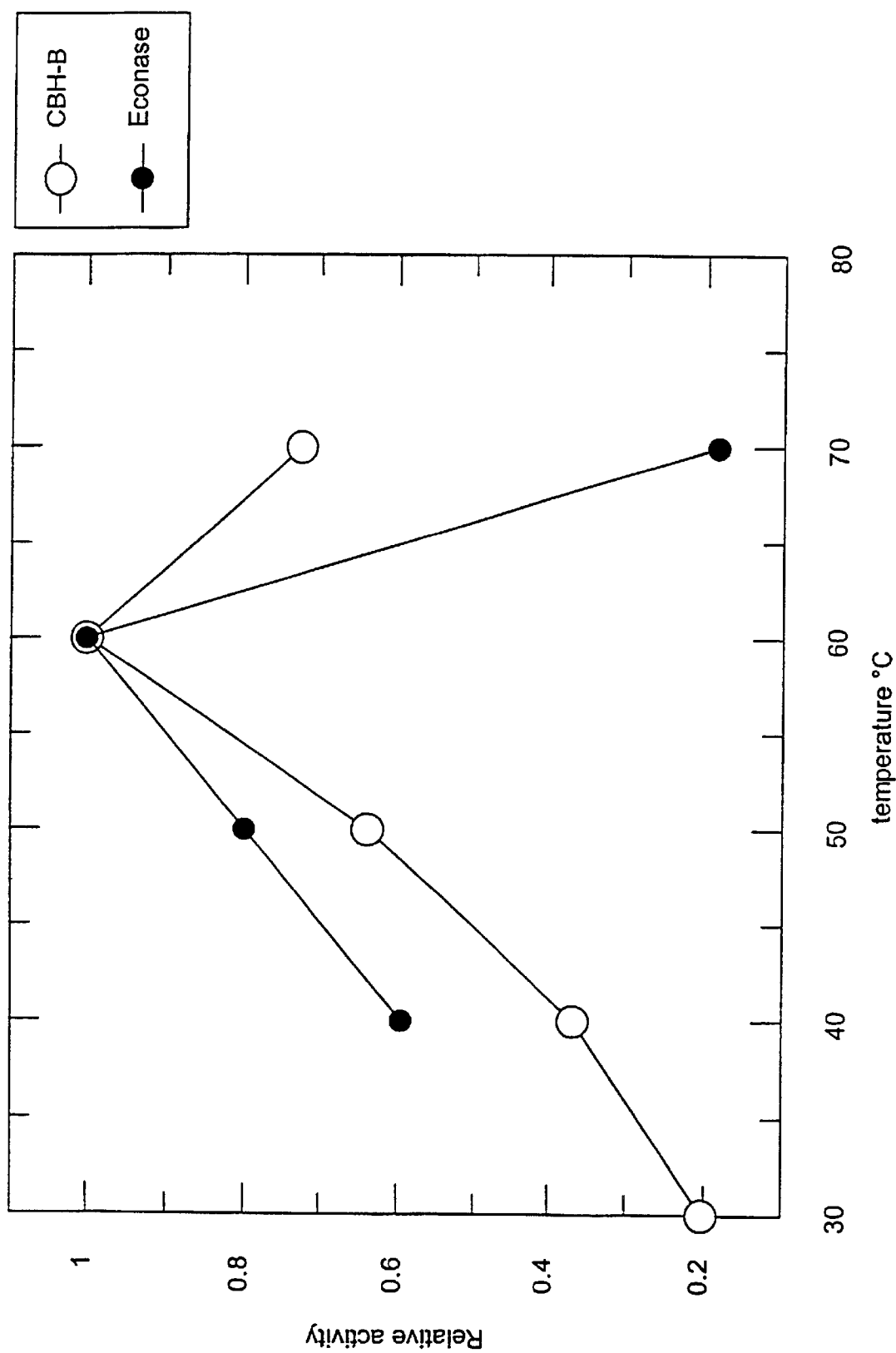
FIG. 3 shows how the activity of CBH B varies with temperature in comparison to Econase.

In FIG. 3 it can be seen that under these assay conditions the temperature optimum of the enzyme is 60° C. Econase also has a temperature optimum at 60° C., but the remaining activity at 70° C. of CBHB is over 70%, whereas the Econase activity at that temperature is less than 10% of the maximum activity.

To determine the pH optimum of CBHB the assay as described above was performed at 40° C., using 100 mM sodium citric acid buffer, set at different pH values. The activity was measured at pH-values ranging from 2.5 up to 6.5.

Figure 4:
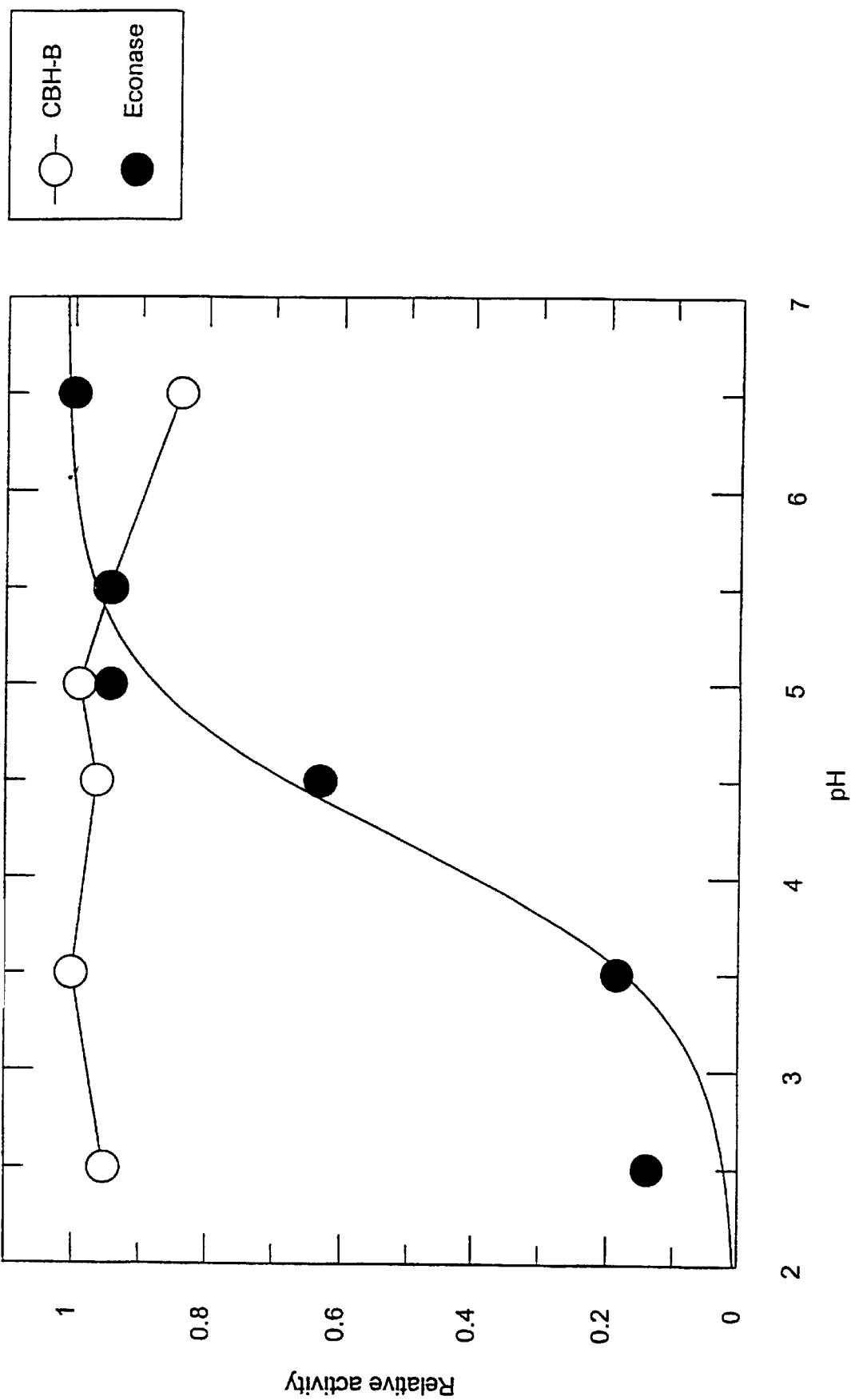
FIG. 4 shows how the activity of CBH B varies with pH in comparison to Econase.

In FIG. 4 it can be seen that the pH profile of CBHB is completely different from the pH profile of Econase. CBHB has more than 80% activity at the whole range from 2.5 to 6.5, whereas below pH 4.5 the Econase activity decrease to below 50%.

Example 6

Baking trial using A. niger CBH

The A. niger CBH of Example 4 was tested in a full scale baking trial using the following recipe:

Flour 2000 g Kolibri (Meneba) & 500 g Ibis (Meneba)
1305 g water
50 g block yeast, Konings gist® (obtainable from Gist-brocades)
50 g salt
12.5 g sugar
25 ppm ascorbic acid
20 ppm Fermizyme® P200 (Fungal a-amylase, obtainable from Gist-brocades)
6.25 mg A. niger CBH from Example 4

After mixing the flour with the ingredients, three 900 gram doughs are fermented. The first fermentation for 30 and the second for 40 minutes at 30° C. and after shaping a final fermentation was for 70 minutes at 35° C. The bread was baked for 30 minutes at 250° C. Thereafter the loaves were allowed to cool and loaf volume was determined by the rape seed displacement method, and other properties were determined. The baking test was carried out as a parallel test in triplicate. The result was a 10% increase in loaf volume, improved dough handling properties and crumb structure, all as compared to a reference where no CBH was added.

REFERENCES

1. Goosen, T., Engelenburg, F. van, Debets, F., Swart, K., Bos, K., Briek, H. van den, (1989) Mol. Gen. Genet. 219: 282–288
2. Harmsen, J. A. M. et al., (1990) Curr. Genet. 18: 161–166.
3. Maniatis T., E. F. Fritsch, J. Sambrook (1982): Molecular cloning, a laboratory manual; Cold Spring Harbor Laboratory, New York.
4. Murray, N.(1977) Mol. Gen. Genet. 150: 53–58
5. Saiki R. K. et al. (1988) Science, 239, 487–491
6. Sambrook, J., Fritsch, E. F., Maniatis, T. (1989) In: Molecular Cloning: a Labatory Manual, 2and edn., Cold Spring Harbor Labatory Press, N.Y.
7. Visniac, W. and Santer, M. (1957), Bact. Rev. 21: 195–213
8. Goosen et al., 1992, "Transformation and Gene Manipulation in filamentous fungi: an overview" In: Handbook of Applied Mycology" Vol. 4: "Fungal Biotechnology",
9. D. K. Arora, R. P. Elander and K. G. Mukerji, eds., Marcel Deker In., New York, pp 151–195 for filamentous fungi
10. Romanos et al., 1992, Yeast 8: 423–488
11. Rosenfeld et al (Rosenfeld J, Cadevielle J, Guillemot J C, Ferrara P (1992) Anal. Biochem. 203, 173–179).

What is claimed is:

1. An isolated polypeptide which has cellobiohydrolase (CBH) activity, and which comprises a sequence at least 80% homologous to a mature protein of SEQ ID No:8 (CBH A) or fragments thereof.

2. The isolated polypeptide according to claim 1, which is produced by *Aspergillus*.

3. The isolated polypeptide of claim 1, which comprises a sequence at least 90% homologous to said mature-protein or fragments thereof.

4. The isolated polypeptide of claim 3, which comprises a sequence at least 95% homologous to said mature protein or fragments thereof.

5. The isolated polypeptide of claim 3, which comprises a mature protein of SEQ. I.D. NO:8.

6. An isolated polypeptide which:.
   (i) has CBH activity;
   (ii) has an activity of at least 50% of the maximum activity over the pH range from 3 to 5;
   (iii) has an optimum activity at a temperature, which is greater than 50° C.; and
   (iv) does not have a cellulose binding domain or a linker peptide.

7. The isolated polypeptide according to claim 6, which has cellobiohydrolase I (CBHI) activity.

8. The isolated polypeptide according to claim 6, which is produced by a fungus.

9. The isolated polypeptide according to claim 8, which is produced by *Aspergillus*.

10. The isolated polypeptide according to claim 9, which is produced by *Aspergillus niger*.

11. A composition comprising a polypeptide according to any one of claim 1, 2 or 6 and at least one additional polypeptide, which is an enzyme.

12. A method to degrade cellulose comprising contacting a polypeptide according to any one of claim 1, 2 or 6 with the cellulose.

13. A method according to claim 12 which is part of a method for producing or processing food or beverages, animal feed, pulp, paper or textiles.

14. A method according to claim 13, wherein:
   (i) the cellulose is contained in a material, which after degradation of all or part of the cellulose within it is used to make a food or beverage for a human or animal, or
   (ii) all or part of the cellulose is degraded after the food is ingested by a human or animal.

15. A method according to claim 13 wherein:
   (i) the cellulose is contained in a material, which after degradation of all or part of the cellulose within it is used to make a food or beverage for a human or animal, and (ii) all or part of the cellulose is degraded after the food is ingested by a human or animal.

16. A bakery product or ingredient, or a baked product obtainable or obtained by a method according to claim 14.

17. A human food or beverage, or animal feed comprising a polypeptide, according to any one of claim 1, 2 or 6.

* * * * *

SEQUENCE LISTING

<160> NUMBER OF SEQ ID NOS: 14

<210> SEQ ID NO 1
<211> LENGTH: 14
<212> TYPE: PRT
<213> ORGANISM: Artificial Sequence
<220> FEATURE:
<223> OTHER INFORMATION: Internal sequence

<400> SEQUENCE: 1

Leu Tyr Leu Met Ser Asp Asp Ser Asn Tyr Glu Leu Phe Lys
1               5                   10

<210> SEQ ID NO 2
<211> LENGTH: 24
<212> TYPE: PRT
<213> ORGANISM: Artificial Sequence
<220> FEATURE:
<223> OTHER INFORMATION: Internal sequence

<400> SEQUENCE: 2

Leu Gly Asn Thr Asp Phe Tyr Gly Pro Gly Leu Thr Val Asp Thr Asn
1               5                   10                  15

Ser Pro Phe Thr Val Val Thr Gln
            20

<210> SEQ ID NO 3
<211> LENGTH: 19
<212> TYPE: DNA
<213> ORGANISM: Artificial Sequence
<220> FEATURE:
<223> OTHER INFORMATION: PCR oligonucleotide

<400> SEQUENCE: 3
gtcggtacca acatggccg                                           19

<210> SEQ ID NO 4
<211> LENGTH: 21
<212> TYPE: DNA
<213> ORGANISM: Artificial Sequence
<220> FEATURE:
<223> OTHER INFORMATION: PCR oligonucleotide

<400> SEQUENCE: 4
actcagaaac attggctata g                                        21

<210> SEQ ID NO 5
<211> LENGTH: 1701
<212> TYPE: DNA
<213> ORGANISM: Aspergillus niger

<400> SEQUENCE: 5
cgaaatcact aaaaggagac gactagagtc ttatacaatc tcattacaat gcatcaacgt    60
gcccttctct tctcagccct gctgacggct gttcgcgccc agcaagccgg aacgctcacg   120
gaggaagtcc atccttcctt gacctggcag aaatgcactt ctgaaggcag ctgcactgaa   180
cagagtggct cagttgtcat tgactcgaac tggcgctgga cccattccgt caatgacagc   240
accaattgct acactggcaa cacctgggat gcaactctct gccctgatga tgagacctgt   300
gcggccaact gcgccctgga cggagcagac tacgagtcca cctacggtgt caccactgac   360
ggtgattcat tgacactgaa attcgtcact ggctccaatg ttggctcgcg gttgtatcta   420
atggacacga gcgacgaggg ataccagacg ttcaacttgc ttgacgcaga gttcactttc   480
gacgttgatg tgtctaacct cccatgtggg ctaaacggcg cgttgtactt cactgcaatg   540
gacgccgatg gtggagtctc aaaataccct gccaataagg ctgcagccaa gtacggaaca   600
ggatactgtg actcccaatg cccccgggac ctgaaattca tcgacggaca agccaacgtc   660
gatggctggg aaccttctag caacaatgac aacacaggta tcggcaatca cggttcttgc   720
tgccctgaaa tggatatctg ggaggcaaac aagatctcga ccgcattgac accccatcct   780
tgtgacagca gcgaacagac catgtgtgag ggtaacgact gcggtggaac ctactcggat   840
gatcgctacg gaggaacctg cgaccctgac ggctgcgact caacccctta tcgcatgggc   900
aacgactctt tctacggtcc tggcaagacc atcgacaccg atccaagat gacggttgtg    960 acccagttca tcactgatgg ctctggctcc ctcagcgaga tcaagcgtta ctacgtgcag  1020
aacggaaatg ttatagcgaa cgctgattcc aacatctctg gagtgactgg aaactcgatc  1080
acaacggact tctgcactgc gcagaagaag gcctttggcg acgaggatat attcgctgag  1140
cacaatggac ttgctggaat cagtgatgcc atgtcttcca tggttctrat cttgagcttg  1200
tgggatgatt actatgccag catggagtgg ctcgacagcg actatcccga gaacgctacc  1260
gctaccgacc caggtgttgc acgcggaaca tgcgactcgg aatcaggcgt ccctgcgaca  1320
gtcgaggggg cgcatcccga ttcttcggtg accttctcaa acatcaagtt cggtcccatc  1380

-continued

```
aactcgacct tcagcgcttc cgcataaggg gaagtgcagg gttcagagcc tcaattacat    1440
cccacaagcc gaacacaaca ggacaggttc ctggaacgga atatgggaga gttgcgggct    1500
tgtaaatagt ccgaaaagtg gtcactgctt ttgtgtatcg ggctgtcttc ccattttatt    1560
ttcattcact ccagattgat tgatgcagat cttgtttgtt gattctttca cttcgtgctg    1620 tgacttttg tacctaactt cacattcgtt tcttttctgt ttttgagtcc actcaatcca    1680
agagaragtt gttcctttgc t                                              1701
```

<210> SEQ ID NO 6
<211> LENGTH: 26
<212> TYPE: DNA
<213> ORGANISM: Artificial Sequence
<220> FEATURE:
<223> OTHER INFORMATION: Oligonucleotide mixture

<400> SEQUENCE: 6
gaygayagya aytaygartt rttyaa    26

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide mixture
<221> NAME/KEY: misc_feature
<222> LOCATION: (1)...(20)
<223> OTHER INFORMATION: n = A,T,C or G

<400> SEQUENCE: 7
gtraanggrc trttngtrtc    20

<210> SEQ ID NO 8
<211> LENGTH: 452
<212> TYPE: PRT
<213> ORGANISM: Aspergillus niger

<400> SEQUENCE: 8

Met His Gln Arg Ala Leu Leu Phe Ser Ala Leu Leu Thr Ala Val Arg
 1               5                  10                  15

Ala Gln Gln Ala Gly Thr Leu Thr Glu Glu Val His Pro Ser Leu Thr
            20                  25                  30

Trp Gln Lys Cys Thr Ser Glu Gly Ser Cys Thr Glu Gln Ser Gly Ser
        35                  40                  45

Val Val Ile Asp Ser Asn Trp Ala Trp Thr His Ser Val Asn Asp Ser
    50                  55                  60

Thr Asn Cys Tyr Thr Gly Asn Thr Trp Asp Ala Thr Leu Cys Pro Asp
65                  70                  75                  80

Asp Glu Thr Cys Ala Ala Asn Cys Ala Leu Asp Gly Ala Asp Tyr Glu
                85                  90                  95

Ser Thr Tyr Gly Val Thr Thr Asp Gly Asp Ser Leu Thr Leu Lys Phe
            100                 105                 110

Val Thr Gly Ser Asn Val Gly Ser Arg Leu Tyr Leu Met Asp Thr Ser
        115                 120                 125

Asp Glu Gly Tyr Gln Thr Phe Asn Leu Leu Asp Ala Glu Phe Thr Phe
    130                 135                 140

Asp Val Asp Val Ser Asn Leu Pro Cys Gly Leu Asn Gly Ala Leu Tyr
145                 150                 155                 160

Phe Thr Ala Met Asp Ala Asp Gly Gly Val Ser Lys Tyr Pro Ala Asn
                165                 170                 175
```

```
Lys Ala Gly Ala Lys Tyr Gly Thr Gly Tyr Cys Asp Ser Gln Cys Pro
            180                 185                 190
Arg Asp Leu Lys Phe Ile Asp Gly Gln Ala Asn Val Asp Gly Trp Glu
        195                 200                 205
Pro Ser Ser Asn Asn Asp Asn Thr Gly Ile Gly Asn His Gly Ser Cys
        210                 215                 220
Cys Pro Glu Met Asp Ile Trp Glu Ala Asn Lys Ile Ser Thr Ala Leu
225                 230                 235                 240
Thr Pro His Pro Cys Asp Ser Ser Glu Gln Thr Met Cys Glu Gly Asn
                245                 250                 255
Asp Cys Gly Gly Thr Tyr Ser Asp Arg Tyr Gly Gly Thr Cys Asp
            260                 265                 270
Pro Asp Gly Cys Asp Phe Asn Pro Tyr Arg Met Gly Asn Asp Ser Phe
        275                 280                 285
Tyr Gly Pro Gly Lys Thr Ile Asp Thr Gly Ser Lys Met Thr Val Val
        290                 295                 300
Thr Gln Phe Ile Thr Asp Gly Ser Gly Ser Leu Ser Glu Ile Lys Arg
305                 310                 315                 320
Tyr Tyr Val Gln Asn Gly Asn Val Ile Ala Asn Ala Asp Ser Asn Ile
                325                 330                 335
Ser Gly Val Thr Gly Asn Ser Ile Thr Thr Asp Phe Cys Thr Ala Gln
            340                 345                 350
Lys Lys Ala Phe Gly Asp Glu Asp Ile Phe Ala Glu His Asn Gly Leu
        355                 360                 365
Ala Gly Ile Ser Asp Ala Met Ser Ser Met Val Leu Ile Leu Ser Leu
        370                 375                 380
Trp Asp Asp Tyr Tyr Ala Ser Met Glu Trp Leu Asp Ser Asp Tyr Pro
385                 390                 395                 400
Glu Asn Ala Thr Ala Thr Asp Pro Gly Val Ala Arg Gly Thr Cys Asp
                405                 410                 415
Ser Glu Ser Gly Val Pro Ala Thr Val Glu Gly Ala His Pro Asp Ser
            420                 425                 430
Ser Val Thr Phe Ser Asn Ile Lys Phe Gly Pro Ile Asn Ser Thr Phe
        435                 440                 445
Ser Ala Ser Ala
        450

<210> SEQ ID NO 9
<211> LENGTH: 1767
<212> TYPE: DNA
<213> ORGANISM: Aspergillus niger

<400> SEQUENCE: 9
gcagtgaatc acaatgtctt ccttccaaat ctaccgagca grtctgctgc tctctatcct    60
tgccactgcc aatgctcagc aggttggcac ctacaccact gagacacatc cgtctctgac   120
ctggcaaacc tgcaccagcg atggcagctg cactaccaac gacggcgagg tggtcatcga   180
cgccaattgg cgttgggtgc actcaacctc cagtgccacc aactgctata ctggcaacga   240
atgggacacc tcaatttgta ccgacgatgt gacctgcgcc gcgaactgcg cgcttgacgg   300
tgccacttac gaggcgacct atggtgtgac cacgtccggc agcgagctgc gcctgaactt   360
cgtcactcaa ggctccagca agaacatcgg gtctcgtttg tacctcatga gcgacgacag   420
caactatgag ctgttcaagc tcctcggcca ggagttcacc tttgatgtcg acgtgtccaa   480
```

```
ccttccctgc ggtctcaacg gcgcgctcta cttcgtcgcc atggacgctg acggtggcac    540
ctcggagtat tccggcaaca aggccggtgc caaatacgga accggctact gcgactcgca    600
gtgccctcgc gacctgaagt tcatcaacgg cgaagccaac tgcgacggct gggagccgtc    660
cagcaacaac gtcaacaccg gagttggcga ccacggctcc tgctgcgccg agatggacgt    720
ctgggaagcg aacagcatct ccaacgcctt chccgcgcac ccctgcgact ccgtcagcca    780
gacaatgtgc gacggtgact cctgtggtgg aacttacagc gccagcggcg accgctacag    840
cggcacctgc gaccccgacg gctgcgacta caaccccntac cgtctaggca cacggactt    900
ttacggcccc ggcctgaccg tcgacacgaa cagccccttc accgtcgtca cccagttcat    960
caccgatgac ggcacctcct ccggcacctt gaccgagatc aagcggttgt acgtgcagaa    1020
cggcgaggtc atcgccaacg gcgcctccac ctactccagt gtcaacggca gctctatcac    1080
ctccgctttc tgtgaatcag agaagacgct gttcggcgac gagaacgtct tcgacaagca    1140
cggcggtctc gagggcatgg gcgaggctat ggccaagggc atggtcttgg tcttgagtct    1200
ttgggatgac tatgccgctg acatgctctg gctcgacagc gactacccg ttaactcgtc    1260
ggcctcgacc cctggtgtgg cccgcggtac ttgtagcacg gactcgggtg tcccggctac    1320
cgtggaggcg gagtcaccca atgcctatgt cacgtactcg aacatcaagt tcgggcctat    1380
tggctcgact tactccagtg gatcttcttc ggggtcgggg tctagctcca gctcgagttc    1440
gactaccact aaggccactt cgacgacctt gaagactacc tcgaccacca gcagtggaag    1500
cagttcgaca tcggcggcgc aggcgtatgg acagtgtggt ggacagggct ggactggtcc    1560
gaccacttgt gtgagtgggt acacttgcac gtatgagaat gcgtactact cgcagtgttt    1620
gtagacacta ctcgaagggg gatgaagatg gcagtgtggg gggggaata gttagtgatt    1680
agtagttagc acacgtacta cagtttagtc aaatttagga agcaatatga catgatcact    1740
tgatgcaaaa aaaaaaaaaa aaaaaaa                                        1767
```

<210> SEQ ID NO 10
<211> LENGTH: 536
<212> TYPE: PRT
<213> ORGANISM: Aspergillus niger

<400> SEQUENCE: 10

```
Met Ser Ser Phe Gln Ile Tyr Arg Ala Ala Leu Leu Ser Ile Leu
  1               5                  10                  15

Ala Thr Ala Asn Ala Gln Gln Val Gly Thr Tyr Thr Thr Glu Thr His
              20                  25                  30

Pro Ser Leu Thr Trp Gln Thr Cys Thr Ser Asp Gly Ser Cys Thr Thr
          35                  40                  45

Asn Asp Gly Glu Val Val Ile Asp Ala Asn Trp Arg Trp Val His Ser
     50                  55                  60

Thr Ser Ser Ala Thr Asn Cys Tyr Thr Gly Asn Glu Trp Asp Thr Ser
 65                  70                  75                  80

Ile Cys Thr Asp Asp Val Thr Cys Ala Ala Asn Cys Ala Leu Asp Gly
                 85                  90                  95

Ala Thr Tyr Glu Ala Thr Tyr Gly Val Thr Thr Ser Gly Ser Glu Leu
            100                 105                 110

Arg Leu Asn Phe Val Thr Gln Gly Ser Ser Lys Asn Ile Gly Ser Arg
        115                 120                 125

Leu Tyr Leu Met Ser Asp Asp Ser Asn Tyr Glu Leu Phe Lys Leu Leu
    130                 135                 140
```

```
Gly Gln Glu Phe Thr Phe Asp Val Asp Val Ser Asn Leu Pro Cys Gly
145                 150                 155                 160

Leu Asn Gly Ala Leu Tyr Phe Val Ala Met Asp Ala Asp Gly Gly Thr
            165                 170                 175

Ser Glu Tyr Ser Gly Asn Lys Ala Gly Ala Lys Tyr Gly Thr Gly Tyr
            180                 185                 190

Cys Asp Ser Gln Cys Pro Arg Asp Leu Lys Phe Ile Asn Gly Glu Ala
            195                 200                 205

Asn Cys Asp Gly Trp Glu Pro Ser Ser Asn Val Asn Thr Gly Val
        210                 215                 220

Gly Asp His Gly Ser Cys Cys Ala Glu Met Asp Val Trp Glu Ala Asn
225                 230                 235                 240

Ser Ile Ser Asn Ala Phe Thr Ala His Pro Cys Asp Ser Val Ser Gln
                245                 250                 255

Thr Met Cys Asp Gly Asp Ser Cys Gly Gly Thr Tyr Ser Ala Ser Gly
            260                 265                 270

Asp Arg Tyr Ser Gly Thr Cys Asp Pro Asp Gly Cys Asp Tyr Asn Pro
            275                 280                 285

Tyr Arg Leu Gly Asn Thr Asp Phe Tyr Gly Pro Gly Leu Thr Val Asp
290                 295                 300

Thr Asn Ser Pro Phe Thr Val Val Thr Gln Phe Ile Thr Asp Asp Gly
305                 310                 315                 320

Thr Ser Ser Gly Thr Leu Thr Glu Ile Lys Arg Leu Tyr Val Gln Asn
            325                 330                 335

Gly Glu Val Ile Ala Asn Gly Ala Ser Thr Tyr Ser Ser Val Asn Gly
            340                 345                 350

Ser Ser Ile Thr Ser Ala Phe Cys Glu Ser Glu Lys Thr Leu Phe Gly
            355                 360                 365

Asp Glu Asn Val Phe Asp Lys His Gly Gly Leu Glu Gly Met Gly Glu
            370                 375                 380

Ala Met Ala Lys Gly Met Val Leu Val Leu Ser Leu Trp Asp Asp Tyr
385                 390                 395                 400

Ala Ala Asp Met Leu Trp Leu Asp Ser Asp Tyr Pro Val Asn Ser Ser
                405                 410                 415

Ala Ser Thr Pro Gly Val Ala Arg Gly Thr Cys Ser Thr Asp Ser Gly
            420                 425                 430

Val Pro Ala Thr Val Glu Ala Glu Ser Pro Asn Ala Tyr Val Thr Tyr
            435                 440                 445

Ser Asn Ile Lys Phe Gly Pro Ile Gly Ser Thr Tyr Ser Ser Gly Ser
450                 455                 460

Ser Ser Gly Ser Gly Ser Ser Ser Ser Ser Ser Thr Thr Lys
465                 470                 475                 480

Ala Thr Ser Thr Thr Leu Lys Thr Thr Ser Thr Thr Ser Ser Gly Ser
                485                 490                 495

Ser Ser Thr Ser Ala Ala Gln Ala Tyr Gly Gln Cys Gly Gly Gln Gly
            500                 505                 510

Trp Thr Gly Pro Thr Thr Cys Val Ser Gly Tyr Thr Cys Thr Tyr Glu
            515                 520                 525

Asp Ala Tyr Tyr Ser Gln Cys Leu
            530                 535

<210> SEQ ID NO 11
<211> LENGTH: 27
<212> TYPE: DNA
```

-continued

```
<213> ORGANISM: Artificial Sequence
<220> FEATURE:
<223> OTHER INFORMATION: PCR oligonucleotide

<400> SEQUENCE: 11
cacaatgcat tccttccaaa tctaccg                                          27

<210> SEQ ID NO 12
<211> LENGTH: 20
<212> TYPE: DNA
<213> ORGANISM: Artificial Sequence
<220> FEATURE:
<223> OTHER INFORMATION: PCR oligonucleotide

<400> SEQUENCE: 12
caccgtcagc gtccatggcg                                                  20

<210> SEQ ID NO 13
<211> LENGTH: 31
<212> TYPE: DNA
<213> ORGANISM: Artificial Sequence
<220> FEATURE:
<223> OTHER INFORMATION: PCR oligonucleotide

<400> SEQUENCE: 13
cctaggatcc tacaaacact gcgagtagta c                                     31

<210> SEQ ID NO 14
<211> LENGTH: 18
<212> TYPE: DNA
<213> ORGANISM: Artificial Sequence
<220> FEATURE:
<223> OTHER INFORMATION: PCR oligonucleotide

<400> SEQUENCE: 14
gttaactcgt cggcctcg                                                    18
```